United States Patent
Roh et al.

(10) Patent No.: US 7,173,062 B2
(45) Date of Patent: Feb. 6, 2007

(54) METHOD FOR THE IMPROVEMENT OF SKIN WRINKLES USING RETINYL RETINOATE

(75) Inventors: Young-Soy Roh, Jeollabuk-do (KR); Soo-Jong Um, Kyunggi-do (KR); Min-Sook Jeong, Jeollabuk-do (KR); Joo-Dong Lee, Kyunggi-do (KR); Hee-Chang Ryoo, Seoul (KR); Jeong-Kuan Son, Kyungsangbuk-do (KR); Hyo-Jung Kim, Incheon (KR); Hyuk Kim, Kyunggi-do (KR); Sung-Won Jung, Incheon (KR); Hye-Sook Han, Seoul (KR); Si-Ho Park, Jeollabuk-do (KR); Seong-Ho Kim, Jeollabuk-do (KR)

(73) Assignee: Enprani Co., Ltd. (KR)

( * ) Notice: Subject to any disclaimer, the term of this patent is extended or adjusted under 35 U.S.C. 154(b) by 308 days.

(21) Appl. No.: 10/466,514

(22) PCT Filed: Jan. 15, 2002

(86) PCT No.: PCT/KR02/00063

§ 371 (c)(1),
(2), (4) Date: Jul. 16, 2003

(87) PCT Pub. No.: WO02/057212

PCT Pub. Date: Jul. 25, 2002

(65) Prior Publication Data

US 2004/0062781 A1    Apr. 1, 2004

(30) Foreign Application Priority Data

Jan. 16, 2001   (KR) ............................... 2001-2292

(51) Int. Cl.
*A61K 31/215*    (2006.01)
(52) U.S. Cl. ...................................... 514/529
(58) Field of Classification Search ............... 424/401; 514/549, 553, 529
See application file for complete search history.

(56) References Cited

U.S. PATENT DOCUMENTS

| 4,126,698 | A | * | 11/1978 | Gander et al. | ............... | 514/549 |
| 4,603,146 | A | * | 7/1986 | Kligman | ..................... | 514/559 |
| 4,757,140 | A | * | 7/1988 | DeLuca et al. | ........... | 536/26.23 |
| 5,043,356 | A | * | 8/1991 | Fulton, Jr. | ................... | 514/549 |

FOREIGN PATENT DOCUMENTS

| EP | 0 271 522 B1 | 10/1993 |
| WO | WO 99/57124 | 11/1999 |

OTHER PUBLICATIONS

Staab, H. A. et al. Ber. 1962, 95, 1284-1297.*

* cited by examiner

*Primary Examiner*—Sreeni Padmanabhan
*Assistant Examiner*—Kevin Capps
(74) *Attorney, Agent, or Firm*—Peter F. Corless; Christine C. O'Day; Edwards Angell Palmer & Dodge LLP

(57) ABSTRACT

The present invention relates to a method for the improvement of skin wrinkles using retinal retaliate.

1 Claim, 2 Drawing Sheets

METHOD FOR THE IMPROVEMENT OF SKIN WRINKLES USING RETINYL RETINOATE

TECHNICAL FIELD

The present invention relates to a retinol derivative and process for the preparation thereof. Particularly, the present invention relates to a novel retinal retaliate of the following formula (1):

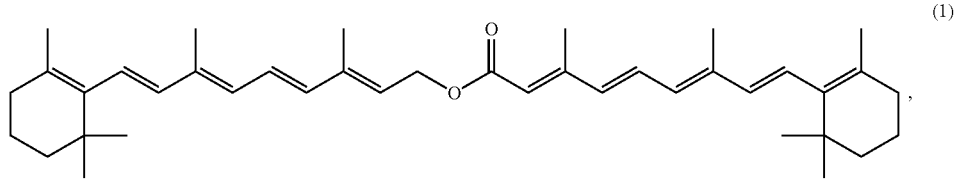

to a process for preparing the same, to a new intermediate that is useful for preparing the same, and to a cosmetic composition comprising the compound of formula (1) as an active ingredient.

BACKGROUND ART

The phenomena of aging are deepened as human beings grow older. Particularly, in the case of skin, the change is remarkable. The main phenomena of the skin aging are increase of wrinkles, thickening, inelasticity, dryness, roughness, spot, etc., which are regarded as being attributed to the exposure to the sunlight over a long time. Such phenomena by the sunlight are called photo-aging and are caused by changes of epidermis and dermis due to the sunlight.

It has been reported that photo-aging of skin may be deterred when a cream containing tretinoin (all-trans-retinoic acid), retinol and derivatives thereof, AHAs, etc. are applied to the skin. However, since tretinoin is fat-soluble, it has little absorbability, and also is unstable in the living body, is irritant to the skin, and may cause some side-effects such as skin dryness, wound, scraping, etc. during the latent period. Therefore, there are many problems in using tretinoin as a main component for medicines and cosmetics (see U.S. Pat. No. 4,677,120). On the other hand, Vitamin A, retinol, can hardly be used because it becomes unstable by light, oxygen, heat, lipid-peroxidation, or water. Therefore, in order to use retinol, additional cost should be paid for stabilizing it by anti-oxidants such as BHT, di-α-tocopherol, BHA, ascorbic acid, tocopheryl linolate, etc., or by adopting some means such as liposome or capsule for intercepting from outside effects (see U.S. Pat. No. 6,221,927 and U.S. Pat. No. 5,744,148). For the reasons as explained above, derivatives thereof having improved stability have been developed. However, the derivatives developed until now are still so unstable when exposed to light that they are converted from a crystalline substance to a viscous one in a short time and are decomposed with some color change and formation of peroxides. As a result, some toxic substances that may give undesirable effects may be formed, which makes the use thereof limited (see U.S. Pat. No. 6,183,774). Meanwhile, it is reported that AHAs have superior stability to Vitamin A and facilitate the collagen synthesis. However, mechanisms of such actions are not accurately elucidated, and thus it is restrictively used due to a concern of skin irritation depending on the pH (see U.S. Pat. No. 6,143,309, U.S. Pat. No. 6,022,896 and U.S. Pat. No. 5,962,015).

Therefore, it is keenly required to develop a material having not only the same activity for deterring skin aging as Vitamin A but also non-irritant property and stability (see U.S. Pat. No. 6,180,670 and U.S. Pat. No. 5,863,942).

DISCLOSURE OF THE INVENTION

In order to meet such needs, the present inventors have extensively studied. As a result, the inventors newly developed a retinal retaliate of the above formula (1) by condensing Vitamin A (retinol) and retinoic acid, each of which has a good effect for anti-wrinkles by itself, and then completed the present invention. The compound of formula (1) developed in the present invention has been identified to have better chemical stability, lower skin irritant property, and higher skin regeneration activity than the previous retinol or retinoic acid.

Therefore, it is an object of the present invention to provide a novel retinal retaliate of formula (1).

It is another object of the present invention to provide a process for preparing the compound of formula (1).

It is still another object of the present invention to provide a novel intermediate compound that can be effectively used for preparing the compound of formula (1) and also can exhibit the effect of deterring skin aging by itself.

It is further another object of the present invention to provide a cosmetic composition for deterring skin aging comprising the compound of formula (1) as the active ingredient.

BEST MODE OF CARRYING OUT THE INVENTION

Figure 1:
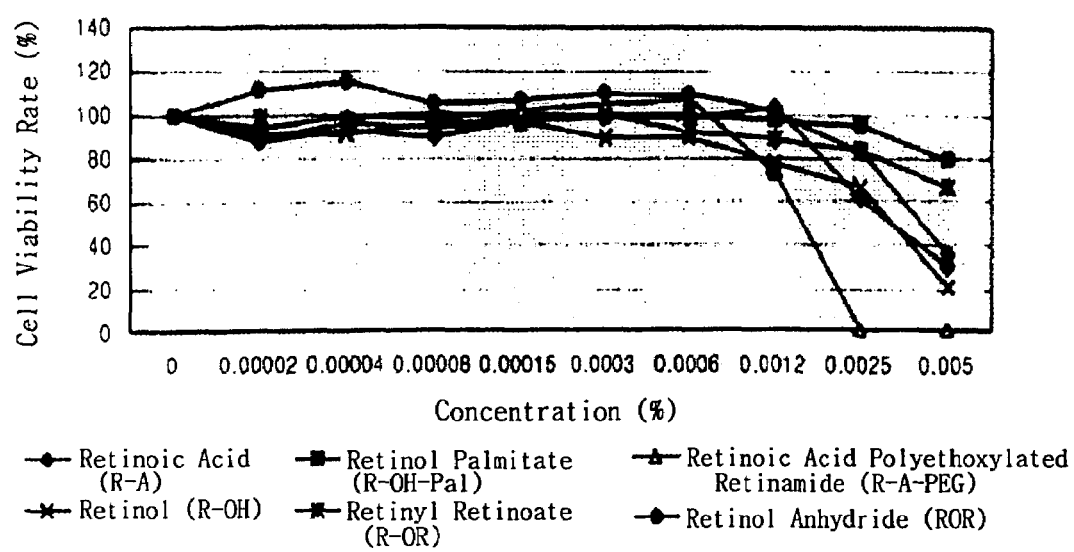
FIG. 1 represents the cell toxicity of the compound of formula (1) according to the present invention compared with the reference materials of retinoic acid, retinol, retinol palmitate, retinoic acid polyethoxylated retinamide and retinol anhydride.

First, the present invention relates to a novel retinal retaliate of the following formula (1):

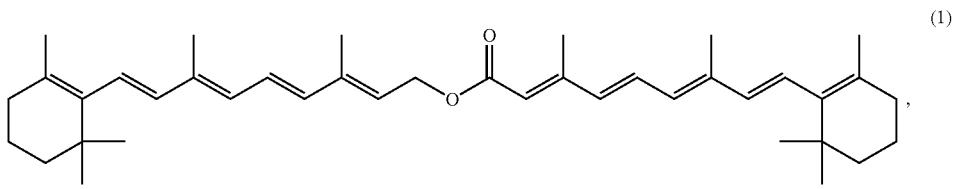

The 13-trans-retinal retaliate of formula (1) of the present invention is not irritant to the skin, exhibits improved activity for collagen synthesis, and also shows a high stability to light (UV light) or heat (high temperature of 40° C. or more).

The present invention also relates to a process for preparing the compound of formula (1).

The compound of formula (1) can be prepared by a process which is characterized in that (a) a compound of the following formula (2a):

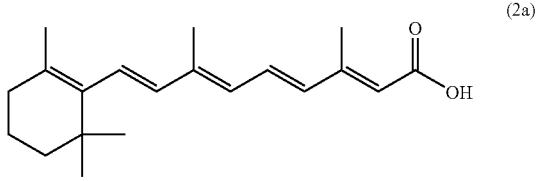

is reacted with a compound of the following formula (3a):

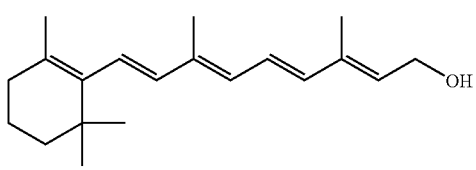

in a solvent and in the presence of a condensing agent and a catalyst;

(b) a compound of the following formula (2b):

is reacted with the compound of formula (3a) in a solvent and in the presence of an organic amine catalyst; or (c) a compound of the following formula (2c):

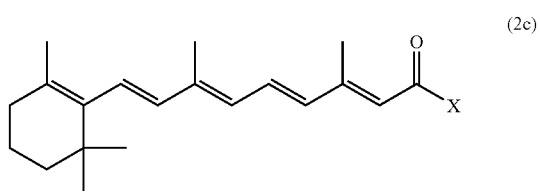

in which X represents halogen, p-toluenesulfonyl or methanesulfonyl, is reacted with the compound of formula (3a) in a solvent and in the presence of an organic amine catalyst.

The above processes according to the present invention will be more specifically explained below.

The condensing agent in Process (a) is N,N-carbonyldiimidazole (CDI), N,N-dicyclohexylcarbodiimide (DCC) or ethylchloroformate, and the catalyst that is used for facilitating the condensation reaction is preferably N,N-dimethylaminopyridine (DMAP) or 1-hydroxybenzotriazole (HOBT). Further, as the reaction solvent, anhydrous organic solvents, such as one or more selected from a group consisting of dichloromethane, benzene, toluene, tetrahydrofuran, and diethylether, can be preferably used. The reaction is typically carried out under nitrogen atmosphere, under the condition for light and moisture to be intercepted, and under the condition of being cooled to warmed.

In Processes (b) and (c), as the organic amine catalyst, those used in the condensation reaction of Process (a) and pyridine or triethylamine can be preferably mentioned. The kinds of usable solvent and reaction conditions are the same as those explained for Process (a).

However, the kinds of base, condensing agent, catalyst, and solvent that can be used in the process according to the present invention are not limited to those as exemplified above, but any one that does not adversely affect the reaction and is conventionally known to the technical field to which

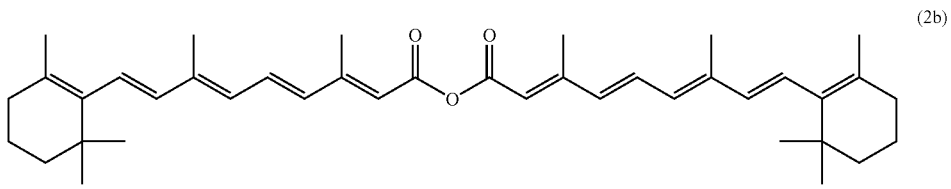

the present invention pertains can be used. Also, the compound of formula (1) prepared by the processes as explained above may be further purified by conventional separation or purification methods, such as recrystallization or column chromatography.

The compound of formula (3a) used as a starting material in the present invention can be easily prepared from a compound of the following formula (3b):

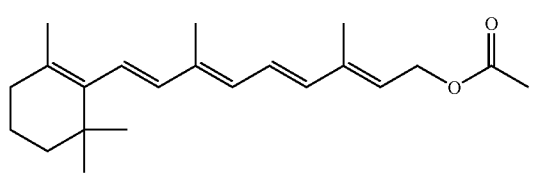

(3b)

by referring to a known method (see U.S. Pat. No. 5,863,942; J. Am. Chem. Soc., 94,8613 (1972)).

Particularly, the retinol anhydride of formula (2b) that is used as a starting material in the process of the present invention itself is a novel compound, and so is another subject matter to be provided by the present invention. The compound of formula (2b) is a useful intermediate for preparing the compound of formula (1), and can also be used as an active ingredient of cosmetic composition for deterring skin aging since it shows an effect of deterring skin aging by itself.

As explained above, the compound of formula (1) according to the present invention is not irritant to the skin, and exhibits an improved activity for collagen synthesis, as well as shows a superior stability to light (UV light) or heat (high temperature of 40° C. or more). Therefore, it can be effectively used as a functional material of cosmetics for deterring skin aging or of medicines for the treatment or prevention of skin troubles including acne, psoriasis, etc. Therefore, the present invention also provides a cosmetic composition comprising the compound of formula (1) as an active ingredient.

More specifically, the compound of formula (1) can be used for the purpose of prevention or improvement of skin aging including wrinkles, freckles, etc. that may be caused by skin cancer or skin troubles such as acne, psoriasis, etc. Particularly, since the compound of formula (1) has a low effective concentration, it can maximize the effect at a low concentration. Further, it shows an excellent stability to the skin due to extremely low cell toxicity, and it has the characteristics of being advantageously used as additives for cosmetics and medicines due to photostability and phase stability under severe and accelerated conditions.

Experiments for demonstrating the physiological activity of the compound of formula (1) may be performed as follows. Cell toxicity of the compound of formula (1) is examined at concentrations ranging from $10^{-6}$ to $10^{-3}$%(W/V) using normal human fibroblast (Newborn), and the skin irritating property is examined by a patch test for the skin of normal adults. Further, the effect of increasing the collagen synthesis in a human fibroblast cell is measured to identify the cell regeneration effect of the compound of formula (1), photostability is identified by measuring $^1$H NMR of the compound of formula (1) after the compound is irradiated by UV light (356 nm) at certain intervals of time, and thermal stability is identified by quantifying the amount at 40° C. (Experiments 1 to 5).

As a result of the above experiments, the compound of formula (1) according to the present invention was identified as being less toxic to cells than retinol, retinoic acid, or other retinol derivatives, each of which was used as commercially available ingredients for medicines and cosmetics for the purpose of deterring skin aging; as being more stable to the human skin than the other retinol analogs; as showing an effect for increasing the collagen synthesis at low concentrations; and as having a long term stability to light or heat differently from the previous retinol derivatives. Therefore, it was confirmed that the compound of formula (1) according to the present invention can be advantageously and conveniently used as an active ingredient for medicines and cosmetics in such forms as cream, lotion, essence, ointment, gel, etc. for the prevention of aging.

The present invention will be more specifically explained in the following examples and experiments. However, it should be understood that the following examples and experiments are intended to illustrate the present invention but not in any manner to limit the scope of the present invention.

Preparation 1: Preparation of the Retinol of Formula (3a)

Potassium carbonate (1.52 g, 0.011 mol) was added to retinol acetate (1.20 g, 0.0036 mol, Roche Co.) dissolved in absolute methanol (30 ml), and the mixture was slowly stirred for 7 hours at room temperature under nitrogen atmosphere and under the condition for light and moisture to be intercepted. The reaction solution was filtered and the solvent was removed by distillation under reduced pressure. The residue was purified by column chromatography (silica gel 60 for cc part, Merk Co., mesh size 270–400, hexane/ethyl acetate=4/1, v/v) to give 1.01 g (Yield 96%) of the pale yellow title compound.

Example 1

Preparation of the Retinal Retaliate of Formula (1)

Retinoic acid (1.26 g, 0.0042 mol, Basf Co.), dicyclohexylcarbodiimide (DCC) (0.87 g, 0.0042 mol) and catalytic amount of dimethylaminopyridine (DMAP) were added to retinol (1.00 g, 0.0035 mol) dissolved in anhydrous dichloromethane (50 ml) at 0° C. The reaction solution was slowly warmed to room temperature and stirred for 12 hours under nitrogen atmosphere and under the condition for light and moisture to be intercepted. The reaction solution was filtered and the solvent was removed by distillation under reduced pressure. The residue was purified by column chromatography (silica gel 60 for cc part, Merk Co., mesh size 270–400, hexane/diethylether=19/1, v/v) to give 1.55 g (Yield 78%) of the pale yellow title compound.

$^1$H NMR (300 MHz, CDCl$_3$) δ 7.03 (dd, 1H, J=26.4 Hz, 11.4 Hz, C$_{20}$H), 6.67 (dd, 1H, J=26.4 Hz, 11.4 Hz, C$_{11}$H), 6.34 (d, 2H, J=2.1 Hz, C$_{19}$H, C$_{12}$H), 6.29 (d, 2H, J=2.1 Hz, C$_7$H, C$_{24}$H), 6.18 (d, 2H, J=9.9 Hz, C$_{23}$H, C8H), 6.12 (d, 2H, J=10.2 Hz, C$_{10}$H, C$_{21}$H), 5.82 (s, 1H, C $_7$H), 5.69 (t, 1H, J=7.2 Hz, C$_{14}$H), 4.81 (d, 2H, J=6.9 Hz, C $_5$H$_2$), 2.39 (s, 3H,

C18CH$_3$), 2.05 (t, 4H, J=5.1 Hz, C$_4$H$_2$, C$_{27}$H$_2$), 2.03 (s, 3H, C$_{13}$CH$_3$), 1.99 (s, 3H, C$_{22}$CH$_3$), 1.94 (s, 3H, C$_9$CH$_3$), 1.74 (s, 6H, C$_5$CH$_3$, C$_{26}$CH$_3$), 1.65 (m, 4H, C$_3$H$_2$, C$_{28}$H$_2$), 1.50 (m, 4H, C$_2$H$_2$, C$_{29}$H$_2$), 1.06 (s, 12H, C1(CH$_3$)$_2$, C$_{30}$(CH$_3$)$_2$)

Preparation 2: Preparation of the Retinol Anhydride of Formula (2b)

Retinoic acid (1.00 g, 0.0033 mol, Basf Co.), dicyclohexylcarbodiimide (DCC) (0.75 g, 0.0036 mol) and catalytic amount of dimethylaminopyridine (DMAP) were added to retinoic acid (1.00 g, 0.0033 mol, Basf Co.) dissolved in anhydrous dichloromethane (50 ml) at 0° C. The reaction solution was slowly warmed to room temperature and stirred for 3 hours under nitrogen atmosphere and under the condition for light and moisture to be intercepted. The reaction solution was filtered and the solvent was removed by distillation under reduced pressure. The residue was purified by column chromatography (silica gel 60 for cc part, Merk Co., mesh size 270–400, hexane/diethylether=19/1, v/v) to give 1.58 g (Yield 82%) of the pale yellow title compound.

$^1$H NMR (300 MHz, CDCl$_3$) δ 7.10 (dd, 2H, J=13.4 Hz, 11.4 Hz, C$_{11}$H, C$_{20}$H), 6.32 (d, 2H, J=16.2 Hz, C$_{19}$H, C$_{12}$H), 6.31 (d, 2H, J=14.7 Hz, C$_{10}$H, C$_{21}$H), 6.18 (d, 2H, J=0.1 Hz, C$_{23}$H, C$_8$H), 6.13 (d, 2H, J=4.5 Hz, C$_7$H, C$_{24}$H), 5.78 (s, 2H, C$_{17}$H, C$_{14}$H), 2.40 (s, 6H, C$_{18}$CH$_3$, C$_{13}$CH$_3$), 2.04 (m, 4H, C$_4$H$_2$, C$_{27}$H$_2$), 2.02 (s, 6H, C$_{22}$CH$_3$, C$_9$CH$_3$), 1.72 (s, 6H, C$_5$CH$_3$, C$_{26}$CH$_3$), 1.62 (m, 4H, C$_3$H$_2$, C$_{28}$H$_2$), 1.47 (m, 4H, C$_2$H$_2$, C$_{29}$H$_2$), 1.03 (s, 12H, C$_1$(CH$_3$)$_2$, C$_{30}$(CH$_3$)$_2$)

Example 2

Preparation of the Retinal Retaliate of Formula (1)

Retinol anhydride (1.00 g, 0.0017 mol) and triethylamine (0.31 g, 0.0021 mol) were added to retinol (0.60 g, 0.0021 mol) dissolved in anhydrous dichloromethane (30 ml) at 0° C. The reaction solution was slowly warmed to room temperature and stirred for 5 hours under nitrogen atmosphere and under the condition for light and moisture to be intercepted. The reaction solution was filtered and the solvent was removed by distillation under reduced pressure. The residue was purified by column chromatography (silica gel 60 for cc part, Merk Co., mesh size 270–400, hexane/diethylether=9/1, v/v) to give 0.91 g (Yield 92%) of the pale yellow title compound. $^1$H NMR data of this compound were the same as those in Example 1.

Example 3

Preparation of the Retinal Retaliate of Formula (1)

Retinoic acid (1.00 g, 0.0033 mol) was dissolved in anhydrous toluene (10 ml) and phosphorus trichloride (PCl$_3$) (0.46 g, 0.0033 mol) was added dropwise thereto. The mixture was stirred for 15 hours at room temperature under nitrogen atmosphere and under the condition for light and moisture to be intercepted. The retinoic acid chloride solution thus obtained was added dropwise together with the retinol prepared in Preparation 1 (0.95 g, 0.0033 mol) and triethylamine (0.61 g, 0.0041 mol) to anhydrous methylene chloride (30 ml) over 20 minutes at 0° C. The reaction solution was then stirred for 5 hours at room temperature. The reaction solution was added to saturated aqueous sodium chloride solution (30 ml). The organic layer was separated, washed with water, dried over sodium sulfate, filtered, and concentrated. The residue was purified by column chromatography (silica gel 60 for cc part, Merk Co., mesh size 270–400, hexane/diethylether=9/1, v/v) to give 1.54 g (Yield 82%) of the pale yellow title compound. $^1$H NMR data of this compound were the same as those in Example 1.

Experiment 1

Cell Toxicity Test

In order to verify the primary stability as a material for medicines and cosmetics, cell toxicity of the retinal retaliate of formula (1) was determined according to MTT method (see: Mossman T., Rapid calorimetric assay for cellular growth & amp;survival:application to proliferation & amp; cytotoxity assays. Journal of Immunological Methods 65, 55–63, 1983) using normal human fibroblast (Newborn) and the results are shown in FIG. 1.

As can be seen from the results of FIG. 1, the compound of formula (1) of the present invention shows a similar cell toxicity to retinol palmitate, but is identified to have a lower intracellular toxicity than retinol, retinoic acid, or derivatives thereof.

Experiment 2

Test for Skin Irritation Property

In order to examine the skin irritation of the compound of formula (1), a patch test for the skin of normal adults was carried out. As the carrier, capryl caprylic triglyceride or the conventional O/W formulation was used, and twenty (20) adults per a group were tested for 24 hours.

The conventional O/W formulation used in the present experiment was prepared according to the following procedure.

Each of the aqueous part of Nos. 1–6 and the oily part of Nos. 7–13 as shown in the following Table 1 was heated to 75–80° C. to be thoroughly dissolved. The oily part was slowly added to the aqueous part and emulsification was performed for 5 minutes at 75–80° C. in a homomixer of 3000rpm. During the emulsification, the mixture was neutralized by the neutralizing agent of No. 14. After the first emulsification, the mixture was cooled, the retinal retaliate and fragrance of Nos. 15–16 were added at 50–55° C., and then the second emulsification was carried out for 3 minutes in a homomixer of 3000rpm. The mixture was cooled again to 27–30° C. to prepare the composition of O/W formulation.

TABLE 1

| | Materials | Content |
|---|---|---|
| Aqueous Part | 1. Distilled water | To 102 |
| | 2. Glycerin | 5.00 |
| | 3. Butylene glycol | 5.00 |
| | 4. Preservative | q.s. |
| | 5. Carbomer | 0.20 |
| | 6. Xanthane gum | 0.05 |
| Oily | 7. Cetostearyl alcohol | 1.0 |

TABLE 1-continued

| | Materials | Content |
|---|---|---|
| Part | 8. Self-emulsifiable monostearic acid glycerin | 1.0 |
| | 9. Monostearic acid sorbitan$_{(1)}$ | 0.5 |
| | 10. Glyceryl monostearate (POE40)$_{(2)}$ | 1.0 |
| | 11. Fluid paraffin | 4.0 |
| | 12. Squalane | 4.0 |
| | 13. Cetyl octanoate | 6.0 |
| Neutralizing Agent | 14. Triethanolamine | 0.2 |
| Additives | 15. Retinyl retinoate | 0.3 |
| | 16. Fragrance | q.s. |

$_{(1)}$Trademark: Ar-60 (ICI, USA)
$_{(2)}$Trademark: My-52 (ICI, USA)

From the experimental results, the irritation indexes were calculated according to the following Equation 1 and the results are represented in the following Table 2.

Irritation index={Σ(Test Value×Number of Examinees Corresponding to the Test Value)/(Total Examinees×The Maximum Test Value)×100   Equation 1

Test Value +++: 5, ++: 4, +: 3, +−: 2, −:1

The degree of irritation was determined according to the following standards:

1.9 or less: Minute irritation, 2.0–2.9: Weak irritation, 3.0–3.9: Moderate irritation, 4.0 or more: Strong irritation

TABLE 2

Results of skin irritation test (Closed Patch Test; 24 hours, 20 adults)

| Sample | Irritation Index | Degree of Irritation |
|---|---|---|
| C.C.T + Retinol (0.075%) | 2.5 | Weak irritation |
| C.C.T + Retinyl Palmitate (0.138%) | 3.8 | Moderate irritation |
| C.C.T + Retinyl Palmitate (0.55%) | 4.5 | Strong irritation |
| C.C.T + Compound of formula (1) (0.075%) | 1.3 | Minute irritation |
| C.C.T + Compound of formula (1) (0.3%) | 1.3 | Minute irritation |
| C.C.T + Compound of formula (1) (0.55%) | 1.3 | Minute irritation |
| C.C.T | 2.5 | Weak irritation |
| O/W Formulation | 2.0 | Weak irritation |
| O/W Formulation + Compound of formula (1) (0.3%) | 2.0 | Weak irritation |

C.C.T = Capryl caprylic triglyceride

From the results of Table 2, it can be seen that the compound of formula (1) of the present invention shows a still lower degree of irritation to the skin than the previous derivatives such as retinol or retinol palmitate.

Experiment 3

Collagen Synthesis Test

Figure 2:
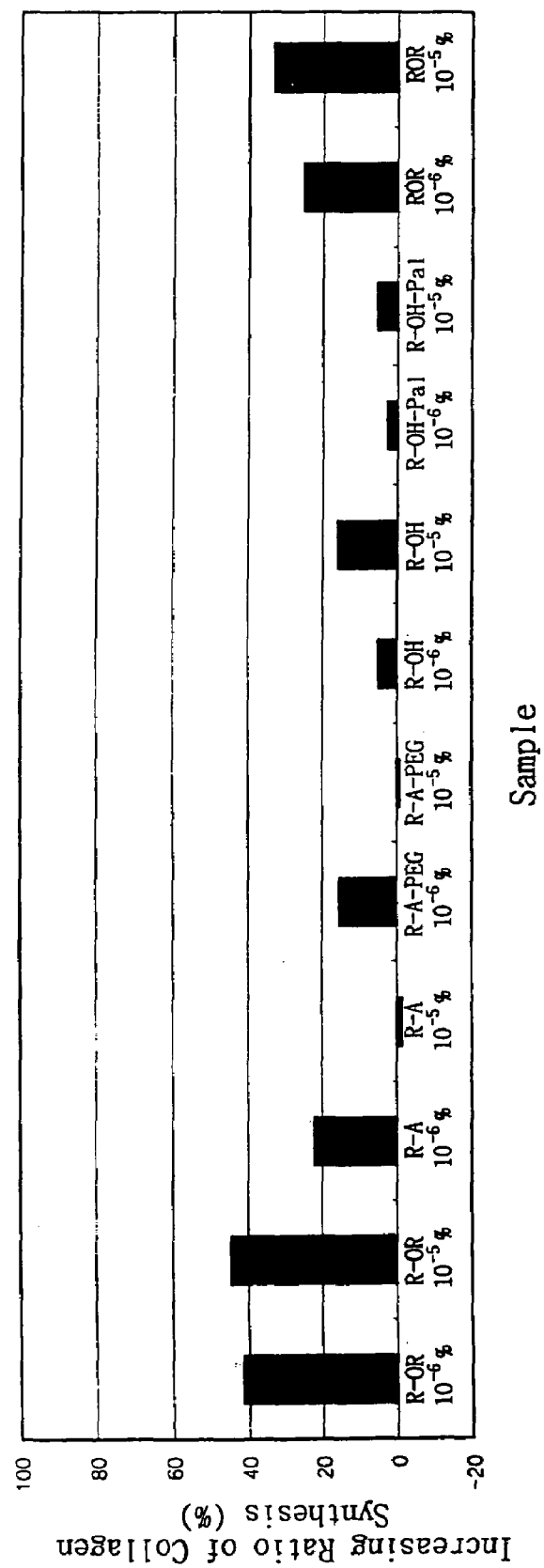
FIG. 2 represents the rate of increase for collagen synthesis by the compound of formula (1) according to the present invention compared with the reference materials of retinoic acid, retinol, retinol palmitate, retinoic acid polyethoxylated retinamide and retinol anhydride (here, R—OR means the retinal retaliate of formula (1) of the present invention; R-A means retinoic acid; R-A-PEG means retinoic acid polyethoxylated retinamide; R—OH means retinol; R—OH-Pal means retinol palmitate; and ROR means the retinol anhydride of formula (2b)).

The effect for collagen synthesis of the compound of formula (1) was examined by using retinol, retinoic acid, and derivatives thereof as comparison compounds to confirm its utility as inhibitors for skin aging as follows. The results are represented in FIG. 2.

The experimental procedure is explained below.

Cell: Normal human fibroblast (Newborn, passage: 6)
Medium: DMEM containing 10% FBS→DMEM free of FBS was used when cells were treated with samples.
Materials: Retinol derivatives, etc.
Concentration: A range of concentration where the samples exert no toxicity to the cells was selected through a cell toxicity test ⇒0.000001%, 0.00001%(w/v)

Procedure: $1 \times 10^5$ cells/well were inoculated into a 6-well plate. Cells were cultured to show about 79–80% confluent. Cells were treated with test samples and incubated for 2 days (FBS was not added to the medium when cells were treated with samples). After 2 days, cell medium and cells were separated from each other and respectively stored in a refrigerator. The cell extract was subjected to the protein analysis (BCA Protein Assay Kit, PIERCE 23225) and the medium was subjected to collagen analysis.

Method for preparing cell extract:

After the medium was removed, a small amount of PBS was added. Cells were scraped with a scraper. 1N NaOH (100 μl) and distilled water (400 μl) were added and the resulting mixture was allowed to stand overnight. Then, the protein analysis was carried out.

Collagen analysis: Analysis kit (Sircol Collagen assay kit—a dye that specifically combines with soluble collagen is used)

Preparation of Test Samples:

1) Reagent blank (0.5M acetic acid or salt/buffer solution 100 μl)

2) Authentic collagen

3) Test sample 100 μl (medium treated with a sample is concentrated—Centricon 10 of Amicon Co. is used)

1.0 ml of Sircol Dye Reagent was introduced into each tube and mixed for 30 minutes. The mixture was centrifuged for 10 minutes at 5,000 g or more and the supernatant was removed. 1.0 ml Sircol Alkali Reagent was added, slowly mixed, and absorbance at 540 nm was measured. The amount of protein was converted into the value of collagen analysis (see: Mechanism of Aging and Development 73, 179–187, 1994).

After the above experiment, the increasing ratio for collagen synthesis of the test group over the control group treated only by DMEM was depicted in FIG. 2. As can be seen from FIG. 2, retinol derivatives such as retinol palmitate show a much lower effect for collagen synthesis than retinol, and retinoic acid derivatives also show a lower effect for collagen synthesis than retinoic acid. In contrast, it was confirmed that the compound of formula (1) of the present invention shows a superior effect for collagen synthesis at low concentration to retinol or retinoic acid. That is, the compound of formula (1) shows an increasing effect of 41.29% at a concentration of $10^{-6}$% (W/V), which is about 10 times as high as the effect of 4.94% shown by retinol at the same concentration.

Experiment 4

Photostability Test

In order to examine photostability of the compound of formula (1) compared with retinol, 10 mg of sample was irradiated by UV-A light (wavelength 356 nm) using a Spectroline (Model CM-10; Fluorescence analysis cabinet; Spectronics Corporation, Westbury, N.Y., USA) at certain intervals of time at room temperature. The results were qualitatively identified by NMR and are represented in the following Table 3.

TABLE 3

Photostability test result

| Sample | After 0 hour | After 2 hours | After 12 hours | After 24 hours | After 48 hours |
|---|---|---|---|---|---|
| Retinyl retinoate | 4 | 4 | 3 | 3 | 3 |
| Retinol | 4 | 3 | 2 | 1 | 1 |
| Retinol anhydride (ROR) | 4 | 3 | 2 | 2 | 2 |

(Level: 4 = No qualitative change in $^1$H NMR spectrum
3 = Minute noise but no qualitative change in $^1$H NMR spectrum
2 = Clear noise and some qualitative change in $^1$H NMR spectrum
1 = Qualitative confirmation is difficult in $^1$H NMR spectrum)

As can be seen from the results of Table 3, the retinal retaliate of the present invention is very stable to UV light having a long wavelength compared with retinol.

Experiment 5

Thermal Stability Test

In order to compare thermal stability of the compound of formula (1) with retinol, phase stability for 1 month in a thermohygrostat (humidity: 58%) of room temperature, 40° C., and 4° C. was examined by a quantitative HPLC analysis under the following condition. The results are represented in the following Table 4.

<HPLC cndition>
1) Column: Capcellpak UG 120 (5 μm, 4.6 mm*150 mm, shiseido, Japan)
2) Mobile phase
Solvent A: Water containing 0.1% acetic acid
Solvent B: Acetonitrile containing 0.1% acetic acid
Solvent C: Methanol containing 0.1% acetic acid
Solvent D: Isopropyl alcohol

| Time (min) | Solvent A | Solvent B | Solvent C | Solvent D | Flow rate (ml/min) |
|---|---|---|---|---|---|
| 0 | 32 | 8 | 60 | 0 | 1.5 |
| 1 | 32 | 8 | 60 | 0 | 1.5 |
| 10 | 2 | 38 | 60 | 0 | 1.5 |
| 11 | 2 | 38 | 60 | 0 | 1.5 |
| 22 | 2 | 48 | 25 | 25 | 1.5 |
| 28 | 2 | 48 | 25 | 25 | 1.5 |
| 29 | 2 | 58 | 0 | 40 | 1.5 |
| 31 | 2 | 58 | 0 | 40 | 1.5 |
| 32 | 32 | 8 | 60 | 0 | 1.5 |
| 40 | 32 | 8 | 60 | 0 | 1.5 |

3) Detector: UV(PDA 326 nm),
Fluorescence: Ex: 326nrm, Em: 460 nm

TABLE 4

Thermal stability test result

| | Retinol | | | Retinyl retinoate | | |
|---|---|---|---|---|---|---|
| | r.t. | 40° C. | 4° C. | r.t. | 40° C. | 4° C. |
| Initial value | 100 | 100 | 100 | 100 | 100 | 100 |
| After 1 week | 74.27 | 56.08 | 100 | 92.77 | 74.46 | 100 |
| After 2 weeks | 65.23 | 43.26 | 98.23 | 90.45 | 70.25 | 100 |
| After 4 weeks | 52.23 | 34.51 | 95.52 | 89.21 | 68.23 | 99.65 |

As is shown in Table 4, the retinal retaliate of formula (1) of the present invention exhibits superior thermal stability to retinol.

Experiment 6

Analysis of Activity for RAR (Retinoic Acid Receptor) or RXR (Retinoid X Receptor)

The effect of the retinol derivatives on the activity of RAR and RXR was examined as follows.

Experimental procedure: Recombinant gene of DR5-tk-CAT or DR1-tk-CAT comprising DR1 or DR5 as a response element of RAR/RXR, thymine kinase promoter, and CAT (chloramphenicol acetyl transferase) was suitably combined with a plasmid DNA that expresses RAR α, β, γ and cotransfected to HaCaT cell line, a skin cancer cell line, with Lipofectamin (GibcoBRL). Then, the cells were incubated in DMEM/10% FBS medium for 1 day, retinol derivative was added in a concentration of 1 μM, and the cells were incubated again for 1 day under the condition of 5% $CO_2$ and 37° C. The cells were washed with phosphate-buffered salione (PBS). Proteins were extracted from each cell, the activity of β-galactosidase was assayed, and the amount of protein was measured to determine the transfection efficiency. Further, the degree of transcription for RAR or RXR was analyzed by CAT ELISA (Roche Molecular Biochemicals, Mannheim, Germany).

Experimental result: As is shown in the following Table 5, the compound of formula (1) of the present invention exhibits a specific activity against RAR cL among the three RARs in the same manner as retinol, and also shows lower activity than retinoic acid but higher one than retinol against RAR β and RAR γ. On the other hand, retinol derivatives such as retinal salicylate and retinal acetyl salicylate show low activity against only RAR α and no activity against RAR βand RAR γ. Further, retinol and the above retinol derivatives show no activity against RXR (α, β, γ), which may be due to the retinol effect.

TABLE 6

Relative activity against RAR/RXR

|  | Control | Retinol | Retinoic acid | Compound of formula (1) | Retinyl salicylate | Retinyl acetyl salicylate |
| --- | --- | --- | --- | --- | --- | --- |
| RAR α | 1.0 | 27.5 | 37.0 | 22.5 | 3.2 | 2.5 |
| RAR β | 1.0 | 1.3 | 4.0 | 1.5 | 1.1 | 1.0 |
| RAR γ | 1.0 | 0.9 | 3.0 | 1.1 | 1.0 | 1.0 |
| RXR α, β, γ | 1.0 | 1.0 | 9.5 | 1.0 | 1.0 | 1.1 |

Conclusion: The compound of formula (1) of the present invention represents in-between properties of retinol and retinoic acid, and thus, shows relatively specific and high activity against RAR α and low activity against RAR β and RAR γ.

Experiment 7: Inhibition of Activity of AP-1 Protein (Activation Protein-1)

AP-1 (comprising c-Jun protein) is a transcription factor inducing the expression of collagenase that is a major cause of skin wrinkles. If retinol derivatives exhibit an inhibitory activity against AP-1, a factor inducing skin wrinkles, they can eventually provide the effect of prevention and treatment of skin wrinkles. Therefore, studies thereabout were carried out in a similar manner to Experiment 6 as follows.

Experimental procedure: CAT reporter (Coll-CAT) having the collagenase promoter wherein AP-1 response element (TRE) is contained, was transfected into HaCaT cell line, a skin cancer cell line, using a liposome. Then, the degree of inhibition against the activity of AP-1 by retinol derivatives was measured through CAT ELISA in a similar manner to Experiment 6. Further, the effect of retinol derivatives on the transcriptional activity of c-Jun (a protein that induces transfer of cancer, skin aging and inflammation, and consists of homologous isomers or heterologous isomers), a constitutional element of AP-1, was examined by cotransfecting c-Jun or RAR α expression vector.

Experimental result: As is shown in the following Table 7, the expression of collagenase inducing skin wrinkles increases as much as about 8.6 times when c-Jun is expressed in a cell. When cells were treated with retinol together with RAR α, the expression of collagenase was inhibited by about 33%. Retinoic acid inhibited by about 64%. It was identified that the compound of formula (1) inhibited by about 52%, an in-between value of the above ones, when cells were treated in the same manner. As expected, retinal acetyl salicylate and retinal salicylate, each of which has no activity against RAR α, exerted no effect on the activity of c-Jun.

TABLE 7

Relative inhibition against the expression of collagenase

| Condition of Expression | — | Retinol | Retinoic acid | Compound of formula (1) | Retinyl acetyl salicylate | Retinyl salicylate |
| --- | --- | --- | --- | --- | --- | --- |
| — | 1.0 | 0.8 | 0.6 | 0.7 | 1.0 | 1.0 |
| c-Jun | 8.6 | 7.3 | 5.4 | 6.7 | 8.5 | 8.7 |
| c-Jun + RAR α | 8.6 | 5.8 | 3.1 | 4.1 | 8.7 | 8.8 |

Conclusion: The above experimental results on the inhibition of AP-1 activity also show that the compound of formula (1) exhibits lower inhibitory activity against c-Jun than retinoic acid, but higher one than retinol, as in Experiment 6.

INDUSTRIAL APPLICABILITY

The compound of formula (1) according to the present invention can be used for the purpose of prevention, improvement, or treatment of skin aging including wrinkles, freckles, etc. that may be caused by skin cancer or skin troubles such as acne, psoriasis, etc. Particularly, since the compound of formula (1) has a low effective concentration, it can maximize the effect at a low concentration. Further, it shows excellent stability to the skin due to the extremely low cell toxicity, and it has the characteristics of being advantageously and conveniently used as additives for cosmetics for prevention and improvement of skin aging and medicines for the treatment of skin troubles such as acne, psoriasis, etc. due to good stability under severe and accelerated conditions.

The invention claimed is:

1. A method for the improvement of skin wrinkles comprising the step of applying a cosmetic composition containing retinyl retinoate of the following formula (I) to skin:

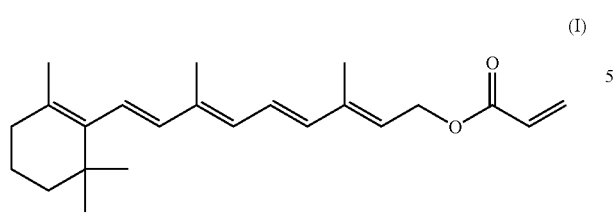
(I)
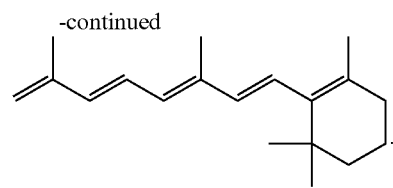
-continued
* * * * *